United States Patent [19]

Chibnik

[11] 4,397,750

[45] Aug. 9, 1983

[54] N-HYDROXYALKYL PYRROLIDINONE ESTERS AS DETERGENT COMPOSITIONS AND LUBRICANTS AND FUEL CONTAINING SAME

[75] Inventor: Sheldon Chibnik, Cherry Hill, N.J.

[73] Assignee: Mobil Oil Corporation, New York, N.Y.

[21] Appl. No.: 291,007

[22] Filed: Aug. 7, 1981

Related U.S. Application Data

[63] Continuation-in-part of Ser. No. 104,483, Dec. 17, 1979, abandoned.

[51] Int. Cl.$^3$ .............................................. C10M 1/32
[52] U.S. Cl. ................................. 252/51.5 A; 44/63; 548/551
[58] Field of Search ................................. 252/51.5 A; 260/326.5 CA, 326.5 FL; 44/63; 548/551

[56] References Cited

U.S. PATENT DOCUMENTS

| | | | |
|---|---|---|---|
| 2,676,949 | 4/1954 | Morner et al. | 252/51.5 A X |
| 2,882,262 | 4/1959 | Smith et al. | 548/551 X |
| 2,945,863 | 7/1960 | Buc et al. | 252/51.5 A X |
| 3,013,975 | 12/1961 | Staker | 252/51.5 A |
| 3,062,631 | 11/1962 | Thompson | 252/51.5 A |
| 3,219,666 | 11/1965 | Norman et al. | 252/51.5 A X |
| 3,734,865 | 5/1973 | Heiba et al. | 252/51.5 A |
| 3,799,877 | 3/1974 | Nnadi et al. | 252/51.5 A X |
| 3,867,405 | 2/1975 | Kanetka et al. | 260/326.5 FL |
| 4,062,786 | 12/1977 | Brois et al. | 252/51.5 A X |
| 4,070,370 | 1/1978 | Elliott et al. | 252/51.5 A X |
| 4,127,493 | 11/1978 | Elliott et al. | 252/51.5 A |

*Primary Examiner*—Andrew Metz
*Attorney, Agent, or Firm*—Charles A. Huggett; Michael M. Gilman; Howard M. Flournoy

[57] ABSTRACT

Esters of hydroxyalkylpyrrolidinones and alkenylsuccinic anhydrides are effective detergent additives for hydrocarbyl lubricants and fuels.

15 Claims, No Drawings

N-HYDROXYALKYL PYRROLIDINONE ESTERS AS DETERGENT COMPOSITIONS AND LUBRICANTS AND FUEL CONTAINING SAME

CROSS REFERENCE TO RELATED APPLICATIONS

This application is a continuation-in-part of application Ser. No. 104,483, filed Dec. 17, 1979 and now abandoned.

BACKGROUND OF THE INVENTION

1. Field of the Invention

This invention relates to novel organic fluids containing minor amounts of hydroxyalkylpyrrolidinone esters useful as detergents, preferably in lubricants comprising oils of lubricating viscosity or greases prepared therefrom, fuels and functional fluids.

2. Description of the Prior Art

U.S. Pat. No. 3,155,685 describes the preparation of lactone-esters from half-esters of alkenylsuccinic anhydrides. It is also known to prepare such esters from alcohols and alkenylanhydrides. U.S. Pat. No. 4,029,675 describes a continuous process for preparing lactone-esters from a branched-chain alkenylsuccinic anhydride and an alcohol or thiol. It is also known to react lactones and amines and thereafter esterify the product so produced with an alkenylsuccinic anhydride. However, there has been no previous disclosure of the present hydroxy pyrrolidinones or their use in lubricants or fuels known to applicant.

SUMMARY OF THE INVENTION

In accordance with the present invention, novel compounds and novel hydrocarbyl fluids selected from the group consisting of lubricating oils, greases, liquid fuels and various functional fluids and a minor amount sufficient to impart detergent and/or dispersant properties thereto of a hydroxy pyrrolidinone prepared by (a) reacting a lactone such as butyrolactone with a hydroxyamine having one or more hydroxy substituents and (b) reacting the intermediate formed from (a) with an alkenylsuccinic anhydride. Equimolar ratios of a lactone and an amino alcohol are preferred for the reaction in (a), although a slight excess, e.g. from about 5 to about 10%, of amino alcohol may be used. The resultant hydroxyamino substituted pyrrolidinone is then reacted in step (b) in a 2 to 1 molar ratio with an alkenylsuccinic anhydride to produce the desired hydroxy pyrrolidinone ester product. However, the molar ratios of the step (b) reactants may be varied respectively from about 1:1 to about 1:10 to produce polymeric products. The process may be briefly summarized with the following illustration:

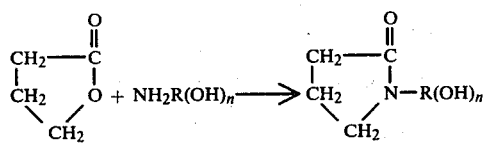

(a)

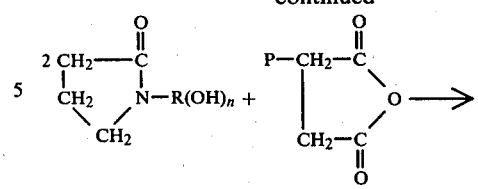

(b)

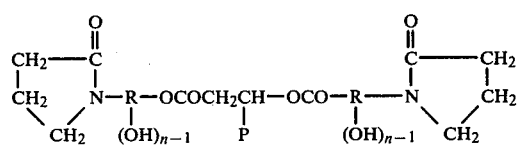

III where n is from 1 to 6, R is alkyl, cycloalkyl or aralkyl of 1 to 30 carbons and P is a polymer such as polyisobutylene of $C_8$–$C_{300}$. Temperatures of from 110° to 300° C. are used in reaction (a), preferably about 180° to about 220° C. Temperatures of from about 110° to about 250° C. are used in reaction (b), with the range of 140° to about 180° C. being preferred. It will be understood that the OH group or groups can be anywhere on the R group. Thus, the pyrrolidinone can also be represented as

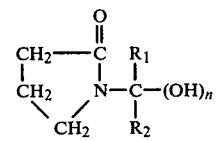

where $R_1$ and $R_2$ are hydrogen alkyl, cycloalkyl, aralkyl or the OH-substituted members thereof. Together with the C linkage, they add up to the stated 1 to 30 carbon atoms for R.

It is to be understood that other hydroxy-amino materials are formed and undoubtedly present during reaction (a) such as oxazolines or hydroxyamides which could, in similar manner to that shown for compound I, react with an alkyl or alkenylsuccinic anhydride to form esterified products. Accordingly the final product will consist substantially of compound III plus crude mixtures of other such reaction products. The ratios of I and II may be varied in any convenient ratio, e.g., from 1:1 to 1:10 or more as stated previously to produce the additive, which may be monomeric, as in III, or polymeric, as in IIIA. The following equation is illustrative thereof:

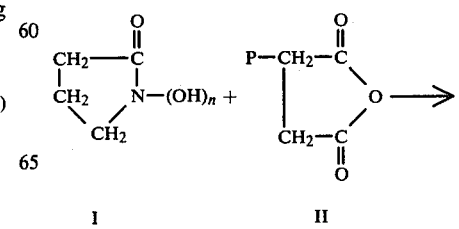

-continued

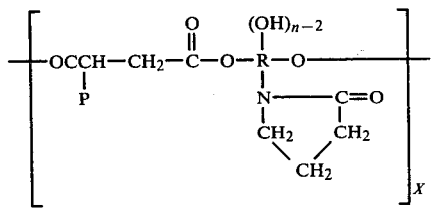

IIIA where R is as defined above, n is equal to or greater than 2 and X indicates repeating polymer groups. It is noted, however, that the specification and the claims are not limited to the molar ratios of reactants illustrated in the exemplary equations.

Suitable lactones include γ-butyrolactone, γ-valerolactone and alkyl, cycloalkyl, aryl and aralkyl substituted-butyrolactones. Especially preferred is γ-butyrolactone.

The hydroxy-substituted primary amines useful in this invention have the formula R—NH$_2$, wherein R is a hydroxy-substituted hydrocarbyl group, preferably alkyl, and contains from 2 to 30 carbon atoms and from 1 to 6 hydroxy groups. Preferably, the hydroxy primary amines contain from 2 to about 20 carbon atoms in a branched form and one or more of the branches contains hydroxy substituents. Hydroxy-substituted alkyl primary monoamines having up to three hydroxyl groups provide highly satisfactory products in accordance with this invention. As stated hereinabove, R may be alkyl, cycloalkyl or aralkyl, and R may also contain other substituents, such as sulfur, oxygen and the like and even additional amino groups. Alkyl and aralkyl sulfide groups and alkyl and aralkyl ether groups may also be present. Preferred hydroxyamines are the primary amines such as 2-aminoethanol, 3-aminopropanol, 2-amino-2-methylpropanol, D, L-2-amino-1-propanol, 2-(2-aminoethoxy)-ethanol and 2-amino-2-ethyl-1-3-propanediol. These primary amines are well known in the art and can be prepared by conventional procedures or obtained commercially when available.

Preferred alkenylsuccinic anhydrides are those conveniently prepared by reacting an olefin or a polymer or oligomer thereof having from 8 to about 300 carbon atoms with maleic anhydride. However, any suitable procedure may be used to obtain alkenylsuccinic anhydrides useful in the present invention. Included among the preferred polymers useful in preparing the anhydride is polyisobutylene having a molecular weight in the range of about 300 to 3000. Such polymers are readily available through normal commercial channels or can be prepared by known methods.

Of particular significance, in accordance with the present invention, is the ability of the compounds to improve the detergency of lubricating media which may comprise liquid hydrocarbon oils in the form of either a mineral oil or a synthetic oil, or in the form of a grease or other solid lubricant in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F., and preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether, phenoxy phenylethers, etc.

It is to be understood, however, that the compositions contemplated herein can also contain other additive materials. For example, corrosion inhibitors, extreme pressure agents, viscosity index agents, antioxidants, anti-wear agents and the like can be used. These materials do not detract from the value of the compositions of this invention, rather these materials serve to impart their customary properties to the particular compositions in which they are incorporated.

Of still further significance, is the detergency improvement of petroleum distillate fuel oils having an initial boiling point from about 75° F. to about 135° F. and an end boiling point from about 250° F. to about 750° F. It should be noted, in this respect, that the term "distillate fuel oils" is not intended to be restricted to straight-run distillate fractions. These distillate fuel oils can be straight-run distillate fuel oils, catalytically or thermally cracked (including hydrocracked) distillate fuel oils, naphthas and the like, with cracked distillate stocks. Moreover, such fuel oils can be treated in accordance with well-known commercial methods, such as acid or caustic treatment, hydrogenation, solvent-refining, clay treatment and the like.

The distillate fuel oils are characterized by their relatively low viscosity and pour point. The principal property which characterizes these hydrocarbons, however, is their distillation range. As hereinbefore indicated, this range will lie between about 75° F. and about 750° F. Obviously, the distillation range of each individual fuel oil will cover a narrower boiling range, falling nevertheless within the above-specified limits. Likewise, each fuel oil will boil substantially, continuously throughout its distillation range.

Particularly contemplated among the fuel oils are Nos. 1, 2, and 3 fuel oils, used in heating and an diesel fuel oils, gasoline, turbine oil and jet combustion fuels. The fuel oils generally conform to the specification set forth in ASTM Specification D396-48T. Specifications for diesel fuels are defined in ASTM Specification D975-48T. Typical jet fuels are defined in Military Specification MIL-F-5624B.

Functional fluids such as hydraulic fluids, heat exchange fluids, transmission fluids, and gear oils and marine diesel oils and fuels such as gasoline and fuel oil may advantageously use the additives of the present invention. Other additives may also be present in these compositions, such as additional detergents, viscosity improvement agents, extreme pressure additives and oxidation stability additives. These additional additives may be ash forming or non-ash forming, including alkenylsuccinimide of alkylene polyamines, metal sulfonates, metal phenates and metal phosphorodithioates. Notably the products of this invention produce no ash and are non-metallic.

The compositions in accordance herewith may contain from 0.05% to about 20% by weight of the said additives and preferably from about 0.1 to 10%. Generally speaking the additives in accordance with the present invention may be effectively used in concentrations ranging from about 0.001 to 10 wt. % with 0.05 to 5 wt. % being preferred.

DESCRIPTION OF SPECIFIC EMBODIMENTS

The following data and examples serve to illustrate the marked degree in detergency improvement of organic media employing the aforementioned esters of hydroxy pyrrolidinones. It is understood, however, that the invention is not limited to the particular embodiments disclosed nor the specific compounds employed as detergent additives. Various modifications thereof can be employed and will be readily apparent to those skilled in the art.

EXAMPLE 1

Preparation of N-(2-hydroxyethyl)-2-pyrrolidinone is described by Puetzer et al., J. Am. Chem. Soc. 74, 4959 (1952). In essence, one mole of γ-butyrolactone is reacted with one mole (or a slight excess) of 2-aminoethanol with partial condensation to allow the water liberated to distill from the reactor. After 5–20 hours at 200° C. an 88% yield of product after distillation is obtained. Unreacted starting materials can be recycled for high ultimate yields if desired.

EXAMPLE 2

In a procedure similar to that of Example 1, 2-amino-2-methylpropanol was reacted with γ-butyrolactone resulting in a 59% yield of N-(1,1-dimethyl-2-hydroxyethyl)-2-pyrrolidinone, b.p. 175°/21 torr, after two cycles. The material melted at 56°-58° with $^{13}$CNMR peaks shifted 176.1, 69.7, 58.7, 46.3, 32.9, 23.2 and 18.2 ppm from TMS. The elemental analyses agreed with the theoretical values for the expected compound.

Found: C, 60.95%, H, 9.38%; N, 9.30%. Calc'd. C, 61.12%; H, 9.62%; N, 8.91%.

EXAMPLE 3

3-aminopropanol reacted in similar manner to Example 2 with butyrolactone furnished a 78.6% yield of N-(3-hydroxypropyl)-2-pyrrolidinone, b.p. 160° C./3 torr.

EXAMPLE 4

2-(2-aminoethoxy)-ethanol reacted in the same manner as Example 1 yielded 75% N-[(2-hydroxyethoxy)ethyl]-2-pyrrolidinone, b.p. 170° C./2.5 torr.

EXAMPLE 5

The reaction product of γ-butyrolactone with 2-amino-2-ethyl-1,3-propanediol reacted as in Example 1 was a dark, viscous material. The infrared absorption spectrum was similar to the other materials in the series with the expected peaks at 3375 cm$^{-1}$ (hydroxyl) and 1660 cm$^{-1}$ (lactam).

EXAMPLE 6

From the reaction of D,L-2-amino-1-propanol with γ-butyrolactone as in Example 1, a 78.6% yield of N-(1-methyl-2-hydroxyethyl)-2-pyrrolidinone, b.p. 142° C./2.5 torr.

Ester detergents in accordance with the present invention were prepared by reacting the hydroxy substituted pyrrolidinones described in certain of the above examples with alkenylsuccinic anhydrides in accordance with the equation denominated hereinabove as equation (b).

EXAMPLE 7

An alkenylsuccinic anhydride prepared from a commercial mixture of $C_{18-24}$ olefins and maleic anhydride (75.5 g, 0.16 moles) was stirred with hydroxyethylpyrrolidinone (Example 1: 47.4 g, 0.37 moles) using a Barrett trap and azeotropic distillation with xylene to remove the water formed. When water collection ceased the solvent was removed under vacuum at 150° C.

EXAMPLES 8–10

The ester detergents of these Examples were prepared like the ester of Example 7 except that the alkenylsuccinic anhydrides of Examples 8, 9 and 10 were respectively prepared from a commercial $C_{36}$ olefin (a dimer of the $C_{18}$–$C_{24}$ mixture of Example 7), polyisobutylene having a molecular weight of 1300 and polyisobutylene having a molecular weight of 900.

EXAMPLES 11–12

Additives of the present invention were prepared like the additive of Example 7, except that the hydroxy substituted pyrrolidinone used was that of Example 5. Also in Example 11 the alkenyl in the alkenylsuccinic anhydride was a 1300 weight polyisobutylene and in Example 12 it was a $C_{36}$ olefin dimer of the $C_{18}$–$C_{24}$ mixture used in Example 8.

EXAMPLE 13

In a manner identical to that of Example 7 a product was made by reacting together the pyrrolidinone of Example 2 and a 900 molecular weight polyisobutylenesuccinic anhydride.

EXAMPLES 14-16

In identical manner to that of Example 7 additives of the present invention were prepared with the exceptions as indicated in the Table.

TABLE

Alkenylsuccinic Anhydride:

$$P-CH_2-\underset{\underset{O}{\|}}{C}\diagdown_{O} \diagup \underset{\underset{O}{\|}}{C}-CH_2$$

Pyrrolidinones:

$$\begin{array}{c} R_1 \quad CH_2OH \\ \diagdown | \\ C \quad O \\ \diagup | \quad \| \\ R_2 \quad N\text{———}C \\ | \quad | \\ CH_2 \quad CH_2 \\ \diagdown \diagup \\ CH_2 \end{array}$$

| Example No. | where P is | $R_1$ | $R_2$ | Mole Ratio, Anhydride/ Pyrrolidinone | Hot Tube Rating |
|---|---|---|---|---|---|
| 7 | $C_{18}$ | H | H | 1/2 | 8 |
| 8 | $C_{36}$ | H | H | 1/2 | 8 |
| 9 | 1300 PB | H | H | 1/2 | 5+ |
| 10 | 900 PB | H | H | 1/2 | 6 |
| 11 | 1300 PB | $C_2H_5$ | $CH_2OH$ | 1/2 | 6+ |
| 12 | $C_{36}$ | $C_2H_5$ | $CH_2OH$ | 1/2 | 6+ |
| 13 | 900 PB | $CH_3$ | $CH_3$ | 1/2 | 8− |
| 14 | 900 PB | $C_2H_5$ | $CH_2OH$ | 1/1 | 5+ |
| 15 | 800 PP | $CH_3$ | H | 1/2 | 4+ |
| 16 | 1300 PB | H | H but the OH has been replaced by $-OCH_2CH_2OH$ | 1/2 | 6 |

$C_{18}$ is a mixture of 18-24+ carbon atoms
$C_{36}$ is a dimer of the above mixture
900 and 1300 PB refer to the molecular weights of a polyisobutylene
PP is polypropylene Several of the hydroxy pyrrolidinone esters of the foregoing examples were individually, 20 parts (non-oil basis), compounded with 947 parts solvent refined SAE 30 grade lubricating oil, 16 parts calcium sulfonate, 4 parts calcium phenate, 10 parts zinc alkyl-dithiophosphate and 1 part acrylic ester polymer and evaluated by the hot tube test described below. The results are shown in Table 1. If no detergent is used, the tube becomes completely clogged with particulate deposits and would have a rating of 10.

HOT TUBE TEST PROCEDURE

Test oil and air are passed upward through a 2 mm capillary tube which is heated with an aluminum block. The test conditions are as follows: 530°-550° F., 10 cc air/minute, 1/3 cc oil/hour, 16 hours. At the end of the test, the tubes are washed with hexane, then rated. A uniform lacquer is deposited in the tube and is rated on a scale of 0-10, with 0 being clean and 10 being heavy black deposits.

As will be seen from the foregoing comparative data and results the compounds in accordance with the present invention impart markedly effective detergent properties to organic compositions.

Although the present invention has been described with preferred embodiments, it is understood that various modifications and adaptations thereof may be made without departing from the spirit and scope of the invention as one of ordinary skill in the art will readily understand.

I claim:

1. A composition comprising a major proportion of a mineral oil of lubricating viscosity synthetic oil of lubricating viscosity, greases prepared from said oils of lubricating viscosity or normally liquid hydrocarbon fuel and a minor amount sufficient to impart detergent and dispersant properties thereto of a hydroxyalkylpyrrolidone ester or polymer thereof wherein said hydroxyalkylpyrrolidinone ester is obtained by reacting, in substantially equimolar amounts, a lactone with a hydroxyamine at a temperature of from about 110° to about 300° C. having the following general formula:

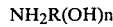

$$NH_2R(OH)_n$$

where R is a hydrocarbyl group having from 1 to about 30 carbon atoms and n is from 1 to about 6 and thereafter esterifying the resulting hydroxyalkylpyrrolidinone product of said reaction with an alkenylsccinic anhydride, at a temperature of from about 110° to about 250° C., wherein the alkenyl group of said succinic anhydride has from about 8 to about 300 carbon atoms, in a molar ratio of from about 1:1 to about 1:10 of said anhydride to said hydroxyalkylpyrrolidinone product.

2. The composition of claim 1 wherein the lactone is selected from the group consisting of γ-butyrolactone, γ-valerolactone and alkyl-, cycloalkyl-, aralkyl- or aryl-substituted butyrolactones.

3. The composition of claim 2 wherein the lactone is γ-butyrolactone.

4. The composition of claim 1 wherein R is $C_2$-$C_{20}$ alkyl and n is from 1 to 3.

5. The composition of claim 4 wherein the hydroxyamine is selected from the group consisting of 2-aminoethanol, 3-aminoethanol, 2-amino-2-methylpropanol, 2-(2-aminoethoxy)-ethanol, D,L-2-amino-1-propanol, 2-amino-2-ethyl-1,3-propanediol, 2-amino-2-methyl-1,3-propanediol and tris(hydroxymethyl)aminomethane.

6. The composition of claim 4 wherein the hydroxyamine is 2-aminoethanol.

7. The composition of claim 4 wherein the hydroxyamine is 2-amino-2-ethyl-1,3-propanediol.

8. The composition of claim 4 wherein hydroxyamine is tris(hydroxymethyl)aminomethane.

9. A compound prepared by (a) reacting under suitable reaction conditions at a temperature of from about 110°-300° C. in substantially equimolar amounts a lactone and a hydroxyamine having the following general formula:

$$NH_2R(OH)_n$$

where R is an alkyl, cycloalkyl or aralkyl group having from 1 to about 30 carbon atoms and n is from 1 to about 6 and thereafter (b) esterifying the resultant hydroxyalkylpyrrolidinone product of reaction (a) at a temperature of from about 110°–250° C. with an alkenyl anhydride wherein the alkenyl group has from about 8 to about 300 carbon atoms in a molar ratio of from about 1:1 to about 1:10 of the pyrrolidinone anhydride to the anhydride.

10. The compound of claim 9 wherein the hydroxyalkylpyrrolidinone is selected from the group consisting of N-(2-hydroxyethyl)-2-pyrrolidinone, N-(1,1-dimethyl-2-hydroxyethyl)-2-pyrrolidinone, N-(3-hydroxypropyl)-2-pyrrolidinone, N-[(2-hydroxyethoxy)ethyl]-2-pyrrolidinone, and N-(1-methyl-2-hydroxyethyl)-2-pyrrolidinone.

11. The compound of claim 9 wherein the alkenyl group is a mixture of olefins containing $C_{18}$ to $C_{24}$, a dimer thereof or polyisobutylene having a molecular weight of from about 300 to about 3000.

12. The compound of claim 9 wherein the pyrrolidinone is N-(1,-1-dimethyl-2-hydroxyethyl)-2-pyrrolidinone and the alkenyl group is a 900 molecular weight polyisobutylene.

13. The compound of claim 9 wherein the pyrrolidinone is the reaction product of γ-butyrolactone and 2-amino-2-ethyl-1,3-propanediol and the alkenyl group is polyisobutylene having a molecular weight of 1300.

14. The compound of claim 9 wherein the pyrrolidinone is the reaction product of γ-butyrolactone and 2-amino-2-ethyl-1,3-propanediol and the alkenyl group is the dimer of a mixture of olefins containing 18 to 24 carbon atoms.

15. A process of preparing a dispersant or detergent additive compound comprising (a) reacting under suitable conditions at a temperature of from about 110°–300° C. in substantially equimolar amounts a lactone with a hydroxyamine having the following general formula:

$$NH_2R(OH)_n$$

where R is alkyl, cycloalkyl, aryl or arylkyl group having from 1 to about 30 carbon atoms and n is from 1 to about 6 and (b) thereafter esterifying the resulting hydroxyalkylpyrrolidinone product of (a) at a temperature of from about 110°–250° C. with an alkenyl anhydride, wherein the alkenyl group has from 8 to 300 carbon atoms in a molar ratio of from about 1:1 to about 1:10 of the pyrrolidinone to the anhydride.

* * * * *

UNITED STATES PATENT AND TRADEMARK OFFICE
CERTIFICATE OF CORRECTION

PATENT NO. : 4,397,750
DATED : August 9, 1983
INVENTOR(S) : SHELDON CHIBNIK

It is certified that error appears in the above—identified patent and that said Letters Patent is hereby corrected as shown below:

Column 1, line 18, change "preferably" to --particularly--.

Column 2, line 16, in Figure III change "(OH)n-1" to --(OH)n$^{-1}$--.

Column 3, line 3, in Figure IIIA, change "(OH)n-2" to --(OH)n$^{-2}$--.

*Signed and Sealed this*

*Fourteenth* Day of *February 1984*

[SEAL]

*Attest:*

GERALD J. MOSSINGHOFF

*Attesting Officer*     *Commissioner of Patents and Trademarks*